(12) United States Patent
Yen

(10) Patent No.: US 9,629,931 B2
(45) Date of Patent: Apr. 25, 2017

(54) NANOPARTICLES FOR THE TREATMENT OF RADIATION SKIN INJURY

(71) Applicant: Richard C. K. Yen, Yorba Linda, CA (US)

(72) Inventor: Richard C. K. Yen, Yorba Linda, CA (US)

(*) Notice: Subject to any disclaimer, the term of this patent is extended or adjusted under 35 U.S.C. 154(b) by 515 days.

(21) Appl. No.: 14/226,544

(22) Filed: Mar. 26, 2014

(65) Prior Publication Data

US 2014/0212358 A1    Jul. 31, 2014

Related U.S. Application Data

(63) Continuation-in-part of application No. 12/927,543, filed on Nov. 16, 2010, now Pat. No. 9,226,898, and a continuation-in-part of application No. 13/560,727, filed on Jul. 27, 2012, and a continuation-in-part of application No. 13/604,770, filed on Sep. 6, 2012, now Pat. No. 9,351,925, and a continuation-in-part of application No. 13/605,765, filed on Sep. 6, 2012.

(60) Provisional application No. 61/853,041, filed on Mar. 27, 2013.

(51) Int. Cl.
| | |
|---|---|
| *A61K 49/00* | (2006.01) |
| *A61K 9/00* | (2006.01) |
| *A61K 9/10* | (2006.01) |
| *A61K 9/14* | (2006.01) |
| *A61K 9/16* | (2006.01) |
| *A61K 38/38* | (2006.01) |

(52) U.S. Cl.
CPC .............................. *A61K 49/0008* (2013.01)

(58) Field of Classification Search
None
See application file for complete search history.

(56) References Cited

U.S. PATENT DOCUMENTS

| | | | |
|---|---|---|---|
| 6,262,019 | B1 | 7/2001 | Keller et al. |
| 6,916,795 | B1 | 7/2005 | Youssef |

OTHER PUBLICATIONS

Dr. Anrei Gudkov, Radiation Sickness Cures and Anti-Radiation Pills, http://nextbigfuture.com/2009/07/radiation-sickness-cures-and-anti.html, Jul. 20, 2009.

*Primary Examiner* — Marsha Tsay
(74) *Attorney, Agent, or Firm* — David A. Guerra

(57) ABSTRACT

The present invention is associated with a method of evaluating platelet function in vivo using skin-irradiation and nanoparticle radiation treatment. The present invention in the recovery of radiation skin injury suggests that radiation skin injury can be used as a substitute model to evaluate platelet substitute products instead of measuring bleeding times. Submicron nanoparticles and a future platelet treatment product are administered intravenously before and after irradiation to subjects. The resultant radiation skin injury are compared and used to evaluate the effectiveness of the platelet treatment product on platelet function in vivo. The radiation skin injury can serve as a model to evaluate platelet and platelet-substitute products, by replacing bleeding time measurements.

16 Claims, No Drawings

NANOPARTICLES FOR THE TREATMENT OF RADIATION SKIN INJURY

CROSS-REFERENCE TO RELATED APPLICATION

This application is a U.S. non-provisional utility application under 35 U.S.C. §111(a) based upon U.S. provisional application 61/853,041 filed on Mar. 27, 2013, and is a continuation-in-part under 35 U.S.C. §120 based upon co-pending U.S. patent application Ser. No. 12/927,543 filed on Nov. 16, 2010, U.S. patent application Ser. No. 13/560,727 filed on Jul. 27, 2012, U.S. patent application Ser. No. 13/604,770 filed on Sep. 6, 2012, and U.S. patent application Ser. No. 13/605,765 filed on Sep. 6, 2012. Additionally, this U.S. non-provisional utility application claims the benefit of priority of U.S. provisional application 61/853,041 filed on Mar. 27, 2013, U.S. patent application Ser. No. 12/927,543 filed on Nov. 16, 2010, U.S. patent application Ser. No. 13/560,727 filed on Jul. 27, 2012, U.S. patent application Ser. No. 13/604,770 filed on Sep. 6, 2012, and U.S. patent application Ser. No. 13/605,765 filed on Sep. 6, 2012. The entire disclosures of the prior applications are incorporated herein by reference.

BACKGROUND OF THE INVENTION

Field of the Invention

The present invention relates to the field of treatment for patients after exposure of their skin to a high dose of ionizing radiation, the treatment resulting in lowered morbidity and mortality of the patient.

Description of the Prior Art

Radiation skin injury is a significant medical and industrial problem. This injury, often referred to as radiation dermatitis, occurs in about 95% of patients receiving radiation therapy for cancer. Workers in a nuclear plant or citizens living near sites with radioactive material may also accidentally come into physical contact with exposed radioactive material as a result of natural disasters or man-made events.

Radiation skin injuries in some ways are different from total body radiation in that the patient's vital organs may be spared (including the bone marrow where new blood cells are to be produced.) However, patients suffering from radiation skin injuries typically also suffer other injuries, the combined effect can be major morbidity and even mortality. In patients suffering from only radiation skin injury, the result ranges in severity: from mild erythema to moist desquamation and ulceration. Currently, there are no effective treatments to prevent the ill effects after radiation skin injury has occurred.

One attempt to mitigate the severity of radiation skin injury was reported by Takikawa M et al. in J Radiat Res. 2012; 53(3):385-94. "Protective Effect of Prostaglandin E1 on Radiation-Induced Proliferative Inhibition and Apoptosis in Keratinocytes and Healing of Radiation-Induced Skin Injury in Rats." They reported that X-irradiation at a dose of 20 Gy induced epilation, minor erosions, and skin ulcers in rats. Prostaglandin E1 has some protective effect only if it is administered 30 minutes to one hour before irradiation. It apparently has no beneficial effect when administered after exposure of the skin to a high dose of radiation. Since few patients know when they will come into contact with a highly radioactive material, this compound is of limited use in realistic situations.

While the above-described devices fulfill their respective, particular objectives and requirements, the aforementioned patents do not describe a nanoparticle radiation treatment that allows treating radiation skin injury.

Therefore, a need exists for a new and improved nanoparticle radiation treatment that can be used for treating radiation skin injury. In this regard, the present invention substantially fulfills this need. In this respect, the nanoparticle radiation treatment according to the present invention substantially departs from the conventional concepts and designs of the prior art, and in doing so provide an apparatus primarily developed for the purpose of treating radiation skin injury.

SUMMARY OF THE INVENTION

In view of the foregoing disadvantages inherent in the known types of skin radiation injury mitigation formulations and system now present in the prior art, the present invention provides an improved nanoparticle radiation treatment, and overcomes the above-mentioned disadvantages and drawbacks of the prior art. As such, the general purpose of the present invention, which will be described subsequently in greater detail, is to provide a new and improved nanoparticle radiation treatment and method which has all the advantages of the prior art mentioned heretofore and many novel features that result in a nanoparticle radiation treatment which is not anticipated, rendered obvious, suggested, or even implied by the prior art, either alone or in any combination thereof.

To attain this, the present invention essentially comprises a method of evaluating platelet function in vivo using skin-irradiation and nanoparticle radiation treatment, the method includes providing submicron nanoparticles, and a platelet treatment product. A predetermined dose of the submicron nanoparticles is administered intravenously to at least one first non-thrombocytopenic subject, and predetermined dose of the platelet treatment product is administered intravenously to at least one second non-thrombocytopenic subject. The first and second non-thrombocytopenic subjects are irradiated to produce radiation skin injury on at least a portion of the first and second non-thrombocytopenic subjects. An amount of radiation skin injury on the portion of the first and second non-thrombocytopenic subjects is determined, and is compared. Then the amount is evaluated to determine an effectiveness of the platelet treatment product on platelet function in vivo.

There has thus been outlined, rather broadly, the more important features of the invention in order that the detailed description thereof that follows may be better understood and in order that the present contribution to the art may be better appreciated.

The invention may also include the step of administering intravenously to at least one fifth and sixth non-thrombocytopenic subjects a predetermined dose of untreated platelets and treated platelets, respectively. The fifth and sixth non-thrombocytopenic subjects are irradiated to produce radiation skin injury on at least a portion of the fifth and sixth non-thrombocytopenic subjects. An amount of radiation skin injury on the portion of the fifth and sixth non-thrombocytopenic subjects are determined and compared. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved nanoparticle radiation treatment that has all of the advantages of the prior art skin radiation injury mitigation formulations and system and none of the disadvantages.

It is another object of the present invention to provide a new and improved nanoparticle radiation treatment that may be easily and efficiently manufactured and marketed.

An even further object of the present invention is to provide a new and improved nanoparticle radiation treatment that has a low cost of manufacture with regard to both materials and labor, and which accordingly is then susceptible of low prices of sale to the consuming public, thereby making such nanoparticle radiation treatment economically available to the buying public.

Still another object of the present invention is to provide a new nanoparticle radiation treatment that provides in the apparatuses and methods of the prior art some of the advantages thereof, while simultaneously overcoming some of the disadvantages normally associated therewith.

Even still another object of the present invention is to provide a nanoparticle radiation treatment for treating radiation skin injury. This allows for the use of submicron albumin particles called nanoparticles, which are coated or not coated with coagulation factors, are effective in reducing the morbidity and mortality associated with radiation skin injury. In addition, the success of the present invention in this injury model suggests that radiation skin injury can serve as a model to evaluate platelet and platelet-substitute products, by replacing, for example, bleeding time measurements.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated embodiments of the invention.

DETAILED DESCRIPTION OF THE INVENTION

Although specific embodiments of the present invention will now be described, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the claims or appended claims.

The present invention deals with treatment of patients exposed to doses of ionizing radiation in high enough doses to cause radiation skin injury, with or without concomitant physical or medical injuries to internal organs or other parts of the body. The present invention is a method of producing submicron nanoparticles, the nanoparticles themselves (coated with coagulation factors and not coated with coagulation factors such as fibrinogen), and the application of nanoparticles intravenously to patients suffering from radiation skin injury or before their exposure to radiation resulting in radiation skin injury.

The present invention has been found to be effective in the mitigation of a number of signs and symptoms related to radiation skin injury. The present invention is effective when given as a prophylactic measure, i.e. administered before the time of exposure to radiation. Significantly, the present invention is also effective when administered at various times after the patient's exposure to high doses of radiation.

Treatment with the present invention reduces the signs and symptoms of radiation skin injury, provided that the treatment is started before the injury becomes irreversible. Often a patient may not even be aware at the time of exposure that he has touched or has been exposed to a highly radioactive substance, because the exposure causes no pain or other sensations. Although the benefit of the present invention may not be fully realized if the treatment is started late, it has been found that at least partial benefits can be realized if the treatment is administered as soon as radiation skin injury is suspected, regardless of which of the various phases of radiation skin injury the patient is going through at the start of the treatment. The time course of radiation dermatitis is well known. Inflammatory erythema develops on the skin within about a week after a high dose of irradiation. The subsequent healing may still result in desquamation and pigmentation. With progressively higher doses of irradiation, blisters may develop, followed by atrophy, teleangiectasia, and irregular hyperpigmentation. With still higher doses of exposure, ulceration occurs, generally within 2 months. Such an ulcer may heal ultimately with severe atrophic scarring. Chronic radiation dermatitis may start within a few months to many years. With some patients, neoplasm may form, the most frequent ones being basal cell carcinoma and squamous cell carcinoma. Therefore, regardless of the dose of radiation to the patient, it is important that the patient be treated with the present invention as soon as possible, before an expected exposure (if possible) and definitely within hours or as soon as possible after the exposure event.

The science of measuring or detecting how much radiation a person has received is still immature. Even if progress can be made soon, it is hard to estimate how much of the radiation has affected the vital organs including the bone marrow, as compared to the radiation having hit less vital parts of the body. A person exposed to radiation on the skin should be regarded as a person who has been exposed to more areas than the skin. Therefore by the time a patient shows signs and symptoms of radiation skin injury, he should be treated for more than the skin injury. In other words, radiation skin injury may serve as an early warning sign that the patient may have been exposed to total-body irradiation: the patient may be in deeper trouble than is shown on the skin. Healthy providers should consider treatment for more severe problems than for the skin alone.

One discovery of the present invention is that the radiation skin injury, when used properly, can serve as an animal model for the evaluation of platelet and platelet-related products. At the present time, the standard clinical method (outside the laboratory and laboratory-obtained blood work results, including measuring the platelet concentration in a blood sample drawn from a patient) to evaluate a patient's ability to form effective hemostatic clots involves the measurement of bleeding time. A cut is made under specific conditions in the skin of a human patient's forearm and the time it takes to form a spontaneous clot is measured. However, the bleeding time is prone to technical variability and errors. The bleeding time is also very difficult to conduct in animals, which are usually used to evaluate a platelet substitute before its application to human patients. The success of the present invention in radiation skin injury indicates that this model can be used to evaluate not only variations of the present invention, but also donor platelets, platelets after different kinds of treatment, and other platelet substitutes. The fact that the present invention is needed to improve the healing process during and after a radiation skin injury shows that the patient's own platelets, regardless of their overall concentration in the body, are not sufficient to overcome the local effects of the radiation injury on the skin. The present invention can serve as a surrogate model to test platelet function in vivo, replacing the bleeding time model.

Experiment One

Manufacture of Submicron-Size Nanoparticles Small Enough to Remain in Suspension for Over a Year at Room Temperature Purpose:

To disclose the method of mass production of a suspension of particles that are essentially spherical and with an average diameter of less than one micron, manufactured from a high concentration of animal albumin.

Material and Method:

Bovine serum albumin powder was purchased from Boval Company LP, Cleburne, Tex. and dissolved in water to result in an 18% solution. The solution will be further processed as follows without the addition of surfactants or detergents. Glutaraldehyde solution was purchased from Sigma-Aldrich, St. Louis, Mo. 63103 and diluted to 0.15 mg per ml with water. An alcohol solution/mixture (containing ethyl alcohol, sodium chloride, glutaraldehyde, all three substance at various concentrations, with the balance being water, hereafter called "EG") was prepared as follows: 2850 ml of 100% ethanol USP grade was mixed with 950 ml of water, after which 7.6 ml of a glutaraldehyde solution (25%) and 114 ml of a sodium chloride solution (0.9%, USP) was added to result in 3921.6 ml of EG solution. Sorbitol powder USP grade was purchased from Sigma-Aldrich and dissolved in water to form a 25% solution. Sodium caprylate was purchased from Jost Chemical Co., St. Louis, Mo. 63114 and dissolved in water to form a 10% solution.

The following steps were done at room temperature, 19° to 24° Centigrade under sterile conditions. All the solutions were filtered via 0.2 micron filters before mixing in a class-100 clean room. At time zero, 190 ml of glutaraldehyde solution (0.15 mg/ml) was added to 381 ml of bovine serum albumin solution (18%) and well mixed in the container. Within 3 minutes, 3426 ml of EG was added and well mixed, at which time the solution turned turbid indicating the formation of spheres.

After one hour, the suspension was dialyzed in distilled water to remove the EG. After measuring the concentration of the spheres in the dialyzed suspension, sorbitol, caprylate and an additional aliquot of distilled water were added to the dialyzed suspension to result in a final concentration, respectively, of 5% sorbitol, 13.3 mg of caprylate per gram of total protein, and 8 mg of spheres/ml of suspension.

The suspension was subsequently filled into sterile containers, capped and sealed. Then the product was terminally sterilized by heating the suspension inside the container to 60° Centigrade for 10 hours, or pressurized up to 600 MPa.

Results:

Analysis of the suspension showed that the particles are spherical and the median diameter was about 0.35 micron, with less than 1% of the spheres with a diameter greater than one micron. No aggregates were observed. The suspension was stable after one year of storage in room temperature without constant agitation to keep the particles in suspension. There was no significant shift of size distribution of particles after one year of storage at room temperature.

The suspension was frozen and kept frozen at minus 18° Centigrade for at least one year. Then samples were thawed and stored at room temperature for at least one year. Analysis of the size distribution of particles showed no significant change from the size distribution of particles in suspensions analyzed within days of completion of synthesis and terminal sterilization.

Comments:

1. Although bovine albumin solutions are used in this experiment, it is anticipated a number of other albumin solutions can be used, including human serum albumin (dialyzed in distilled water, or not dialyzed), other natural (human or animal) albumin or albumin molecules produced by recombinant-DNA methods. In addition, other proteins may be used to produce spheres with comparable functionality, including fibrinogen, immunoglobulin, collagen, gelatin, as disclosed in U.S. Pat. No. 5,069,936 by Yen incorporated herein by reference.

2. Although the spheres are not further coated with any other biologically active molecules during the manufacturing process in this experiment, it is anticipated that a number of other biologically active molecules, including coagulation factors, such as fibrinogen, vonWillebrand factor, Factor IX and other coagulation factors may be added to the spheres during the manufacturing process. It is expected that various ratios of mixing of the biologically active molecule solution with the sphere suspension is permissible. Specifically, experiments have been conducted where, for example, a solution of fibrinogen up to 3 mg/ml may be mixed at a ratio of 1 part (by volume) of the fibrinogen solution to 4 parts (by volume) of the sphere suspension (the turbid suspension after addition of EG, and before dialysis of the EG-containing suspension with distilled water) to result in "coated spheres." See PCT/US2008/006014 by Yen incorporated herein by reference.

3. Although a specific concentration of ingredient solutions are mentioned here as an example, other higher or lower concentrations can be used when combined with a compatible compensating concentration of other ingredients. For example, albumin solutions can vary between 5% to 20% in initial concentration before the addition of a glutaraldehyde solution, which can vary from 0.05 to 0.5 mg/ml. The concentration of ethanol in the EG mix can vary from 55% to 100%, while the glutaraldehyde concentration in EG can vary from 0.1 mg to 0.75 mg/ml and the sodium chloride concentration can vary from 0.5 to 0.005 mg/ml in the EG mix.

4. It was unexpected that a suspension of protein spheres can undergo heating at 60° Centigrade for 10 hours without forming aggregates or clumps. The addition of sorbitol together with caprylate probably has a synergistic effect on protecting the protein spheres from aggregation or expression of new antigenic sites during the process of heating and subsequent cooling to room temperature.

Experiment Two

Improvement in Healing Rates and Healing Results by Treatment with Submicron Particles in Rats Irradiated with a High Dose of Ionizing Radiation which Results in Radiation Skin Injury Purpose:
To find out (a) if any dose of the submicron particles (not coated with any active biological molecules) can improve the rate of healing in the skin in rats exposed to a dose of radiation sufficient to cause radiation skin injury, and (b) whether the results of the healing process are improved with treatment compared to natural healing without the present invention.

Material and Method:
Submicron nanoparticles were synthesized as in Experiment One without the addition of fibrinogen or any other biologically active molecules during the manufacturing steps, except that human serum albumin (8% solution) is used instead of bovine serum albumin (18%.)

Sprague Dawley rats were used, 10 rats per group. Test articles (12 mg of submicron particles per kg for all the injections) and control solution (a 5% sorbitol solution, given at the equivalent volume as the test article per kg weight of the animal) were administered intravenously to animals before or after irradiation, as follows:

Group One: Two doses of submicron particles administered before irradiation (on day−2, and day−1);

Group Two: Two doses of control solution administered before irradiation (on day−2, and day−1);

Group Three: Two doses of submicron particles administered after irradiation (on day+1 and day+2);

Group Four: Two doses of control solution administered after irradiation (on day+1, and day+2);

Group Five: No treatment with test article or control solution: irradiation control.

The radiation dose was 30 Gy gamma rays, delivered to one hind leg. The study endpoint was acute skin toxicity. The rats were euthanized at 30 days post irradiation. Onset of skin toxicity (transient erythema, dry or moist desquarmation, thinning of the dermal tissue, dermal atrophy and necrosis), their severity and the rate of healing were recorded, with observations made daily.

Results:
The results showed that the rats in Group Two, Group Four and Group Five all showed severe radiation skin injury on the irradiated leg. There was no radiation skin injury on the other, non-irradiated leg. The on-set of radiation skin injury in Group One and Group Three were delayed and in some rats negligible. The severity of radiation skin injury in Group One and Group Three, if any, was noticeably less severe than the comparison Group Two and Group Four. The result of healing was noticeably better in Group One and Group Three when compared to Group Two and Group Four, respectively: there was no noticeable formation of atrophy, teleangiectasia, and irregular hyperpigmentation. The results in Group Four (treatment given after irradiation) was comparable to that in Group Two (treatment before irradiation).

Comments:
1. Submicron particles administered intravenously to animals exposed to high doses of ionizing radiation on the skin improved their healing rate, and reduced morbidity during the healing process (including possibly less pain or chance of infection). The result of the healing process appears to be superior to that resulting from natural healing without the application of the present invention. More experiments need to be done to see if a higher dose or lower dose of the nanoparticles will provide further improvement, and whether different schedules of administration (for example, given only once at day−1, or given once on day+1) or given later than day+2 after exposure to radiation will have similar or better protective effects. Given the fact that submicron particles have long in vivo effective life span, it is expected that doses given 5 days before exposure to radiation can be effective. It is also expect that doses of submicron particles given after 5 days after exposure to radiation can be effective.

2. Although this experiment used submicron particles not coated with fibrinogen or other biologically active molecules, it is anticipated that submicron particles pre-coated with biologically active molecules during the synthesis steps may be equally effective, or even better.

3. The exact mechanism of protection is not clear from this experiment. Given the complexity of radiation skin damage, it is expected that there are multiple mechanisms, each perhaps contributing in some way toward a synergistic effect. Therefore, it is expected that other products produced in a manner different from the present disclosure may be also effective in achieving the same end of improving survival rate after a massive dose of radiation. For example, products that have undergone the following steps may also be effective via mechanisms different or similar to those exerted by the presently-disclosed invention: the steps may involve the addition of surfactants or detergents, mixing with an emulsifier, spray drying, exposure to air/liquid interface stress, heat-fixation to render the particles stable against resolubilization in vitro or in vivo. In addition, particles that may not be essentially spherical in shape or with average diameter less than one micron and less than 1% of the particles being larger than one micron may also be effective. Particles containing air and particles that exert their biological effects with a requirement to bind additional biological molecules through free functional groups such as amine, hydroxyl, carboxyl or sulfhydryl groups may also be effective.

4. It is expected that similar results in all mammalian species, including the rabbit, the mouse, the dog, the cat, the horse, all non-human primates and all human patients. It is possible that non-mammalian species, such as reptiles, birds and fish can have similar responses to the beneficial effects of the present invention.

5. The long shelf life of the present invention suspension of submicron particles makes this product an outstanding candidate for stockpiling in areas where radioactive chemicals or radioactive materials are stored or used. During and after a disaster, there will not be the usual number of healthy providers who can provide medical care. The sooner a suspected victim is treated, the sooner he will be able to help others rather than staying as a burden. Therefore, even though this present invention is effective long after the time of exposure, it is expected the treatment to start as soon as a subject is suspected to have been exposed to the radiation.

6. The science of detecting/measuring how much radiation a patient has received and whether the dose has been delivered to vital organs including the bone marrow is still immature. All patients who show radiation skin injury (whether the patient is aware of the exposure or not) should be treated as if he has received radiation affecting more than the skin. In other words, the signs and symptoms of radiation skin injury should be taken as an early warning that the patient might have suffered more severe exposure and in other parts of the body other than on the skin alone. If a dosing regimen or dosage can be shown to result in less morbidity and in improved survival after total body irradiation, the physician should consider using that dosing regimen or dosage, i.e. treating the more severe irradiation problems (possibly total-body exposure) in addition to the treatment of radiation skin injury.

Experiment Three

Comparison of Various Products in their Effectiveness in Improving the Healing Rates and Healing Results from Radiation Skin Injury. The Products Include: (A) Untreated Donor Platelets, (B) Treated Donor Platelets, (C) Nanometer-Sized Albumin Particles Purpose:

(a) To compare the effectiveness of nanoparticles of the present invention with that of donor platelets (without treatment) and donor platelets after their treatment with a viral-inactivation procedure.

(b) To evaluate if nanoparticles are useful as substitutes for donor platelets.

(c) To evaluate a new method to assess in vivo platelet function: using the radiation skin injury as a model for the evaluation of novel platelet substitute compounds and products.

Material and Method:

Submicron particles (nanoparticles of this invention) were synthesized as in Experiment One except that fibrinogen is added to the blank spheres to coat the spheres before the excipients are added. In addition, human serum albumin (8% solution) is used instead of bovine serum albumin (18%).

Donor platelet concentrates were purchased from a local blood bank. Methods of treating platelets with chemicals to inactivate potential contamination from infectious agents had been published, e.g. P. H. Ruane et al. "Photochemical inactivation of selected viruses and bacteria in platelet concentrates using riboflavin and light" in Transfusion 2004 June; 44(6):877-85. A similar method was used in association with the present invention.

New Zealand White rabbits were used in this radiation skin injury model, 10 animals per group. Samples of blood were drawn immediately before irradiation. All the clotting parameters and cell concentrations, including platelets, are within normal limits.

Series One of this experiment evaluated the nanoparticles of the present invention. Test articles (24 mg of submicron particles per kg) and control solution (a 5% sorbitol solution, given at the equivalent volume as the test article per kg weight of the animal) were administered intravenously to animals before or after irradiation, as follows:

Group One: One dose of submicron particles administered before irradiation (on day−3);

Group Two: One dose of control solution administered before irradiation (on day−3);

Group Three: One dose of submicron particles administered after irradiation (on day+3);

Group Four: One dose of control solution administered after irradiation (on day+3);

Group Five: No treatment with test article or control solution: irradiation control.

Series Two evaluated untreated donor platelet concentrates. Five groups were evaluated as in Series One above. An adequate dose of untreated platelets was administered to the animals intravenously on day−3 (in group one) and day+3 (in group three) instead of albumin nanoparticles.

Series Three evaluate platelet concentrates that had been treated to inactivate infectious agents. Five groups were used as in Series One above. An adequate dose of treated platelets was administered to the animals intravenously on day−3 (in group one) and day+3 (in group three) instead of albumin nanoparticles.

Results:

The results were similar to those in Experiment Two. Essentially, the animals in Group Two, Group Four and Group Five all showed severe radiation skin injury on the irradiated leg. There was no radiation skin injury on the other, non-irradiated leg. The on-set of radiation skin injury in Group One and Group Three were delayed. The severity of radiation skin injury in Group One and Group Three, if any, was noticeably less severe than the respective comparison Group Two and Group Four. The result of healing was noticeably better in Group One and Group Three when compared to Group Two and Group Four, respectively: there was no noticeable formation of atrophy, teleangiectasia, and irregular hyperpigmentation. The results in Group Four (treatment given after irradiation) was comparable to that in Group Two (treatment before irradiation).

The results in Series One were comparable to those in Series Two and in Series Three. There was no statistically significant difference between the results of Series Two when compared to Series Three.

Comments:

Bleeding Time (BT) has been used as the golden clinical test to evaluate in vivo platelet function of a patient. It provides the physician an idea how thrombocytopenic is a patient or how inactivated are the patient's platelets. BT is prolonged when the platelet concentration in a patient is less than normal, or when his platelets are inactivated, e.g. by medication. However, BT is difficult to perform. It is highly dependent on the skill of the technician. In small animals it is technically even more difficult to perform than in a human patient. Therefore there is need for another system which can be used to evaluate platelet function in vivo.

These experiments have demonstrated that it is not necessary to generate a thrombocytopenic animal in order to assess platelet substitutes. There is no need to reduce overall platelet concentration in vivo or suppress platelet function in vivo, in order to assess the efficacy of a new product which is designed to augment platelet function or serve as platelet substitutes. The fact that the present invention can improve healing from radiation skin injury whether the overall platelet concentration in the animal is within the normal range or not, shows that the overall platelet concentration is not sufficient to overcome the injury at the local level at the skin. The improvement by the present invention in the recovery of radiation skin injury (compared to control) suggests that radiation skin injury can be used as a substitute (or surrogate) model to evaluate platelet substitute products instead of measuring bleeding times.

While embodiments of the nanoparticle radiation treatment have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those described in the specification are intended to be encompassed by the present invention. And although treating radiation skin injury has been described, it should be appreciated that the nanoparticle radiation treatment herein described is also suitable for other radiation injuries or traumas.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of evaluating platelet function in vivo using skin-irradiation and nanoparticle radiation treatment, said method comprising the steps of:
   a) providing submicron albumin particles having a diameter less than one micron;
   b) providing a platelet treatment product;
   c) administering intravenously to at least a first non-thrombocytopenic subject a predetermined dose of the submicron nanoparticles;
   d) administering intravenously to at least a second non-thrombocytopenic subject a predetermined dose of the platelet treatment product;
   e) irradiating the first and second non-thrombocytopenic subjects to produce radiation skin injury on at least a portion of the first and second non-thrombocytopenic subjects;
   f) determining an amount of radiation skin injury on the portion of the first and second non-thrombocytopenic subjects;
   g) comparing the amount of radiation skin injury between the first and second non-thrombocytopenic subjects; and
   j) evaluating an effectiveness of the platelet treatment product on platelet function in vivo.

2. The method according to claim 1 further comprising the steps of:
   providing at least one control non-thrombocytopenic subject;
   irradiating the control non-thrombocytopenic subject to produce radiation skin injury on at least a portion of the control non-thrombocytopenic subject;
   determining an amount of radiation skin injury on the portion of the control non-thrombocytopenic subject; and
   comparing the amount of radiation skin injury between the first, second, and control non-thrombocytopenic subjects.

3. The method according to claim 2, wherein step c) is performed prior to the irradiating of the first non-thrombocytopenic subject.

4. The method according to claim 3, wherein step d) is performed prior to the irradiating of the second non-thrombocytopenic subject.

5. The method according to claim 4 further comprising the steps of:
   irradiating at least a third non-thrombocytopenic subject to produce radiation skin injury on at least a portion of the third non-thrombocytopenic subject;
   administering intravenously to the third non-thrombocytopenic subject a predetermined dose of the submicron nanoparticles after the irradiating of the third non-thrombocytopenic subject;
   determining an amount of radiation skin injury on the portion of the third non-thrombocytopenic subject; and
   comparing the amount of radiation skin injury between the first, second, third and control non-thrombocytopenic subjects.

6. The method according to claim 5 further comprising the steps of:
   irradiating at least a fourth non-thrombocytopenic subject to produce radiation skin injury on at least a portion of the fourth non-thrombocytopenic subject;
   administering intravenously to the fourth non-thrombocytopenic subject a predetermined dose of the platelet treatment product after the irradiating of the fourth non-thrombocytopenic subject;
   determining an amount of radiation skin injury on the portion of the fourth non-thrombocytopenic subject; and
   comparing the amount of radiation skin injury between the first, second, third, fourth and control non-thrombocytopenic subjects.

7. The method according to claim 6 further comprising the steps of:
   administering intravenously to at least a fifth non-thrombocytopenic subject a predetermined dose of untreated platelets;
   irradiating the fifth non-thrombocytopenic subject to produce radiation skin injury on at least a portion of the fifth non-thrombocytopenic subject;
   determining an amount of radiation skin injury on the portion of the fifth non-thrombocytopenic subject; and
   comparing the amount of radiation skin injury between the first, second, fifth and control non-thrombocytopenic subjects.

8. The method according to claim 7 further comprising the steps of:
   administering intravenously to at least a sixth non-thrombocytopenic subject a predetermined dose of treated platelets;
   irradiating the sixth non-thrombocytopenic subjects to produce radiation skin injury on at least a portion of the sixth non-thrombocytopenic subject;
   determining an amount of radiation skin injury on the portion of the sixth non-thrombocytopenic subject; and
   comparing the amount of radiation skin injury between the first, second, fifth, sixth and control non-thrombocytopenic subjects.

9. The method according to claim 8, wherein the untreated platelets are administered to the fifth non-thrombocytopenic subject prior to the irradiating of the fifth non-thrombocytopenic subject.

10. The method according to claim 9, wherein the treated platelets are administered to the sixth non-thrombocytopenic subject prior to the irradiating of the sixth non-thrombocytopenic subject.

11. The method according to claim 10 further comprising the steps of:
   irradiating at least a seventh non-thrombocytopenic subject to produce radiation skin injury on at least a portion of the seventh non-thrombocytopenic subject;

administering intravenously to the seventh non-thrombocytopenic subject a predetermined dose of the untreated platelets after the irradiating of the seventh non-thrombocytopenic subject;

determining an amount of radiation skin injury on the portion of the seventh non-thrombocytopenic subject; and comparing the amount of radiation skin injury between the first, second, fifth, sixth, seventh and control non-thrombocytopenic subjects.

12. The method according to claim 11 further comprising the steps of:

irradiating at least an eighth non-thrombocytopenic subject to produce radiation skin injury on at least a portion of the eighth non-thrombocytopenic subject;

administering intravenously to the eighth non-thrombocytopenic subject a predetermined dose of the treated platelets after the irradiating of the eighth non-thrombocytopenic subject;

determining an amount of radiation skin injury on the portion of the eighth non-thrombocytopenic subject; and comparing the amount of radiation skin injury between the first, second, fifth, sixth, seventh, eighth and control non-thrombocytopenic subjects.

13. The method according to claim 1, wherein the submicron particles are produced from animal albumin.

14. The method according to claim 1, wherein the submicron particles are produced from an animal albumin solution, a glutaraldehyde solution, an alcohol solution containing ethyl alcohol sodium chloride, glutaraldehyde and water (EG solution), and a sodium caprylate solution.

15. The method according to claim 14, wherein the submicron particles are produced by:

mixing a predetermined amount of the glutaraldehyde solution to the animal albumin solution in a container;

mixing the EG solution to the glutaraldehyde and the bovine serum albumin solutions in the container to produce a suspension;

dialyzing the suspension to remove the EG solution and to produce a dialyzed suspension; and adding the sodium caprylate solution to the dialyzed suspension to produce a resultant suspension.

16. The method according to claim 15 wherein the resultant suspension is filled into at least one sterile container and sterilized by heating the sterile container to a predetermined temperature, at a predetermined pressure, and for a predetermined amount of time.

* * * * *